United States Patent
Ota

(10) Patent No.: US 6,533,774 B1
(45) Date of Patent: Mar. 18, 2003

(54) LASER DEPILATION APPARATUS

(75) Inventor: Yasuo Ota, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/512,285

(22) Filed: Feb. 24, 2000

(30) Foreign Application Priority Data

Feb. 26, 1999 (JP) ............................................. 11-050660
Feb. 26, 1999 (JP) ............................................. 11-050661

(51) Int. Cl.⁷ ............................................. A61B 18/18
(52) U.S. Cl. .............................. 606/9; 606/10; 606/11; 606/12; 607/89; 607/91
(58) Field of Search ................................ 606/8–13, 16, 606/127; 607/88–94; 128/898

(56) References Cited

U.S. PATENT DOCUMENTS

| | | | |
|---|---|---|---|
| 4,388,924 A | 6/1983 | Weissman et al. | |
| 4,617,926 A | 10/1986 | Sutton | |
| 5,059,192 A | 10/1991 | Zaias | |
| 5,209,748 A | 5/1993 | Daikuzono | |
| 5,226,907 A | 7/1993 | Tankovich | |
| 5,425,728 A | 6/1995 | Tankovich | |
| 5,853,407 A | 12/1998 | Miller | |
| 5,879,346 A | 3/1999 | Waldman et al. | |
| 6,162,211 A | * 12/2000 | Tankovich et al. | 606/9 |
| 6,162,212 A | * 12/2000 | Kreindell et al. | 606/9 |
| 6,273,883 B1 | * 8/2001 | Furumoto | 606/9 |
| 2001/0056237 A1 | * 12/2001 | Cane et al. | 600/475 |

FOREIGN PATENT DOCUMENTS

| | | |
|---|---|---|
| EP | 0 788 814 | 8/1997 |
| EP | 0 880 941 | 12/1998 |
| JP | 6-509734 | 11/1994 |
| JP | 11-332879 | 12/1999 |
| JP | 2000-501016 | 2/2002 |
| WO | WO 95/03089 | 2/1995 |
| WO | WO97/35526 | 10/1997 |
| WO | WO 98/55180 | 12/1998 |
| WO | WO 99/07438 | 2/1999 |

* cited by examiner

Primary Examiner—Linda C. M. Dvorak
Assistant Examiner—Ahmed Farah
(74) Attorney, Agent, or Firm—Finnegan, Henderson, Farabow, Garrett & Dunner, L.L.P.

(57) ABSTRACT

A laser depilation apparatus for performing depilation on a skin by irradiating the skin with a laser beam is disclosed. The apparatus includes a first irradiation unit including a laser source (21) for emitting a laser beam for depilation and a light delivery optical system (22, 23, 28, 2, 3) for forming the depilation laser beam emitted from the laser source into a small spot and delivering the beam into a first predetermined range (30) to irradiate the range; a first detection unit (6, 25) for detecting a position of a portion to be depilated within at least the first range; and a controller (20) for controlling the first irradiation unit to selectively irradiate the position of the portion to be depilated with the depilation laser beam based on detection result of the first detection unit.

8 Claims, 4 Drawing Sheets

LASER DEPILATION APPARATUS

BACKGROUND OF THE INVENTION

1. Field of the Invention

The present invention relates to a laser depilation apparatus for performing depilation or hair removal on a skin with a laser beam.

2. Description of Related Art

Heretofore, there has been known laser depilation in which a laser beam is irradiated to hair roots or hair papillae in a shaved skin in order to cauterize them for depilation. The hair roots, hair papillae, and hair follicles that are the peripheries of the hair roots and papillae contain a larger amount of melanin than the surrounding epidermis. Laser light of wavelengths likely to be absorbed into melanin is irradiated, and resultant heat energy is temporarily accumulated in the melanin and then radiated to the hair roots and papillae. The hair roots and papillae are thus cauterized.

However, a conventional laser depilation apparatus is configured such that a laser beam whose diameters range from 10 to 20 mm is irradiated to a skin portion to be depilated. All the hair roots and papillae in the irradiated region are then cauterized. Since melanin contained in the epidermis also absorbs a laser beam, the epidermis in the irradiated region is greatly damaged. If the power of a laser beam or the irradiation time thereof is reduced too greatly in efforts to alleviate the damage to the epidermis, depilation may not be partly achieved or the time required for the procedure may be prolonged. This is inefficient.

The conventional laser depilation apparatus needs that, for cauterizing hair roots, the power of a laser beam, the irradiation time thereof, and other irradiation conditions are determined in consideration of a difference of the thickness of one hair root from that of another. How the irradiation conditions are determined depends largely on an operator's experience. If the power of a laser beam is too strong or the irradiation time thereof is too long, the epidermis is damaged. In contrast, if the power of a laser beam is too weak or the irradiation time thereof is insufficient, a laser-irradiated range in the skin is not depilated reliably and efficiently.

SUMMARY OF THE INVENTION

The present invention has been made in view of the above circumstances and has an object to overcome the above problems and to provide a laser depilation apparatus capable of alleviating the damage to epidermis of a skin and performing efficient depilation on the skin.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser depilation apparatus for performing depilation on a skin by irradiating the skin with a laser beam, the apparatus including first irradiation means including a laser source for emitting a laser beam for depilation and a light delivery optical system for forming the depilation laser beam emitted from the laser source into a small spot and delivering the beam into a first predetermined range to irradiate the range; first detection means for detecting a position of a portion to be depilated within at least the first range; and control means for controlling the first irradiation means to selectively irradiate the position of the portion to be depilated with the depilation laser beam based on detection result of the first detection means.

According to another embodiment of the present invention, there is provided a laser depilation apparatus for performing depilation on a skin by irradiating the skin with a laser beam, the apparatus including: first irradiation means including a laser source for emitting a laser beam for depilation and a light delivery optical system for delivering the depilation laser beam emitted from the laser source into a first predetermined range to irradiate the range; detection means for detecting thickness of a hair existing within at least the first range; irradiation condition setting means for variably setting an irradiation condition of the depilation laser beam based on detection result of the detection means; and control means for controlling the first irradiation means based on the irradiation condition set by the irradiation condition setting means.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of one preferred embodiment of a laser depilation apparatus embodying the present invention will now be given referring to the accompanying drawings.

Figure 1:
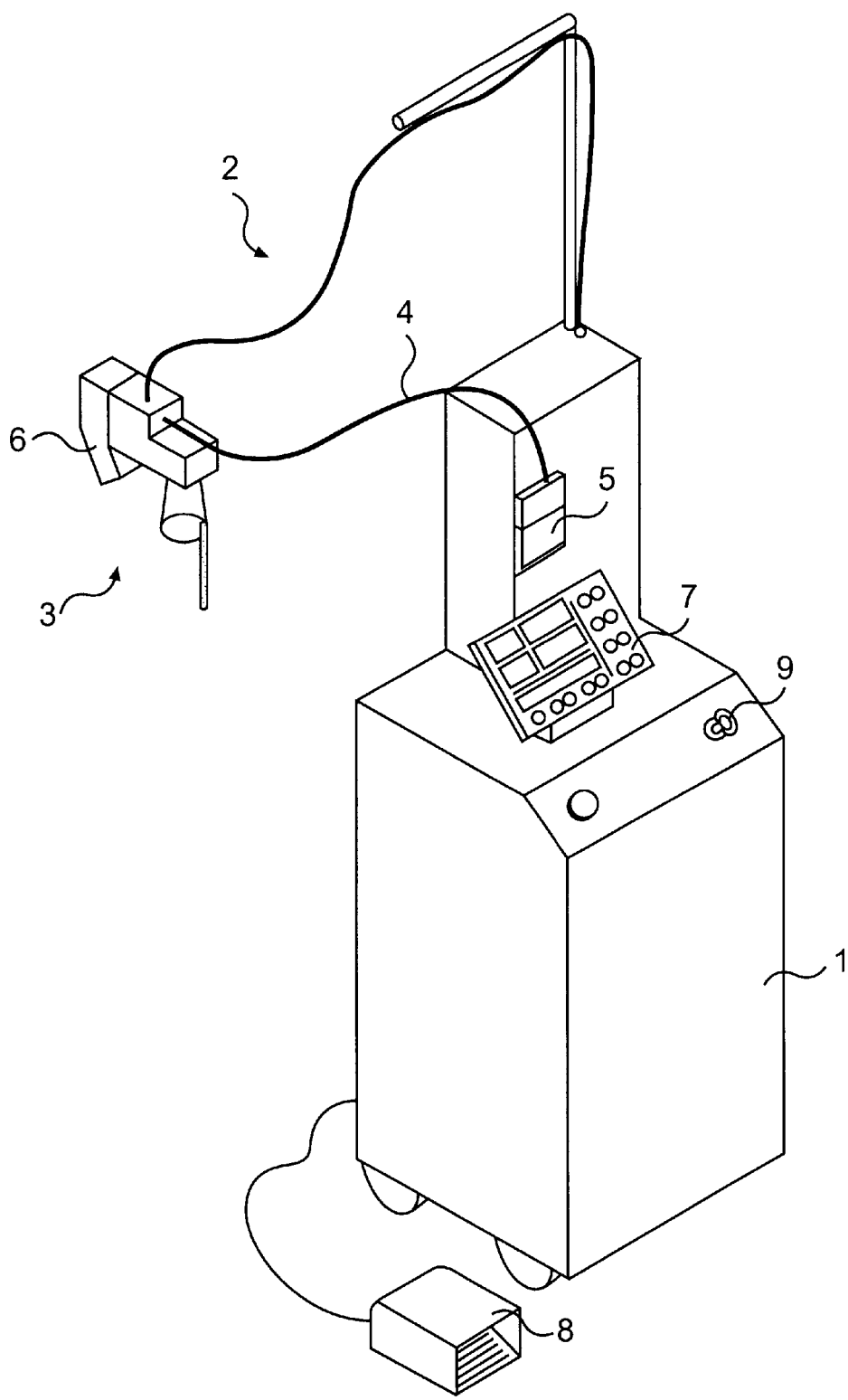
FIG. 1 is a perspective view of a laser depilation apparatus in an embodiment according to the present invention.

FIG. 1 is a perspective view of a laser depilation apparatus in the present embodiment.

Reference numeral 1 denotes a main unit of the laser depilation apparatus, in which a controller 20, a laser source 21, and other elements (see FIG. 3) mentioned later are contained. Reference numeral 7 denotes a control panel used for inputting various setting conditions such as laser irradiation conditions. Reference numeral 8 denotes a foot switch for generating a trigger signal to start the emission of a laser beam (for depilation) of the laser source. Reference numeral 9 denotes a key switch for turning on the power of the apparatus.

Reference numeral 2 denotes an optical fiber for delivering a laser beam emitted from the main unit 1. Reference numeral 3 denotes a hand-piece unit with a laser irradiation outlet. This hand-piece unit 3 is provided with a thermograph 6 including a CCD camera 6a (see FIG. 3) sensitive to infrared rays. The thermograph 6 is used for detecting, before depilation, positions of hair follicles (i.e., positions of hair roots) and sizes thereof (i.e., thicknesses of hair roots) according to a difference in temperature of the skin surface to be depilated. The detecting method will be mentioned later in detail.

Figure 2:
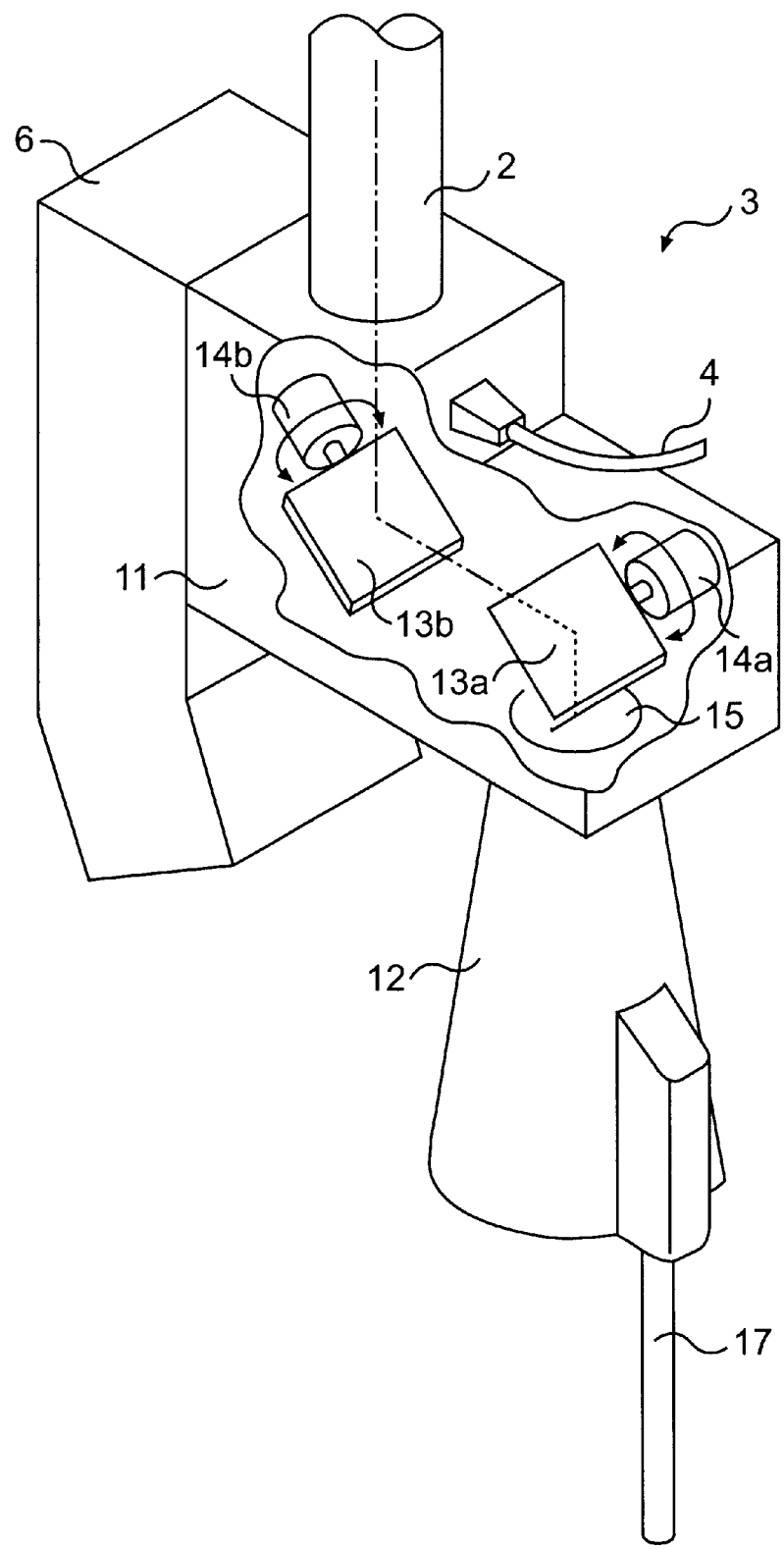
FIG. 2 is a perspective view of a hand-piece unit of the apparatus in the embodiment.

FIG. 2 is a perspective view of the hand-piece unit 3. This hand-piece unit 3 is constructed of a scanner section 11 and a head section 12. In the scanner section 11, provided is a lens 10 (see FIG. 3) for forming the laser beam passed through the optical fiber 2 into a small spot having a diameter which falls within a range of about 1–2 mm on an irradiated portion. The scanner section 11 is further provided with driven mirrors 13a, 13b for scanning the laser beam in two-dimensional directions (X- and Y-directions), drive motors 14a, 14b for driving the motors 13a, 13b respectively, and a lens 15 which is laid on or removed from an optical path of the laser beam. In the present embodiment, a galvano-mirror is used for a set of a driven mirror and a drive motor; the mirror 13a and the motor 14a, and the mirror 13b and the motor 14b.

The lens 15 is inserted and held on the optical path at the time of detection of the positions of hair follicles and then diffuses the laser beam on the skin surface. A drive motor 16 (see FIG. 3) is activated to insert/remove the lens 15 onto/from the optical path. The head section 12 is provided with a pole 17 serving as a tip end of the head section 12. During operation, the pole 17 is abutted on the skin for stably holding the hand-piece unit 3. It is to be noted that a range (region) to be irradiated is determined according to a swing angle of the mirrors 13a, 13b and a height from the laser irradiation outlet of the hand-piece unit 3 to the skin to be irradiated.

Figure 3:
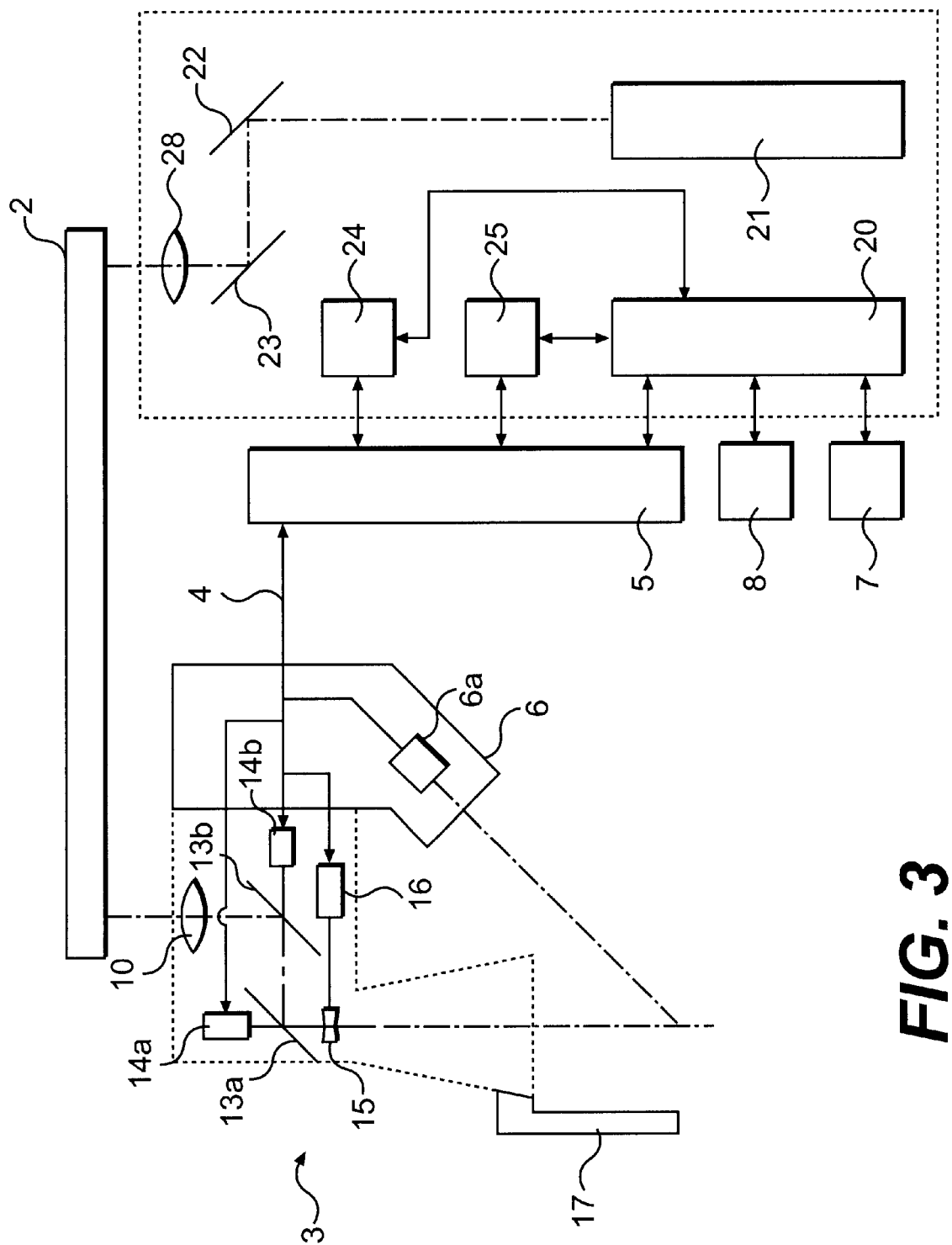
FIG. 3 is a block view of an optical system and a control system of the apparatus in the embodiment.

FIG. 3 is a block diagram of main elements of a control system and an optical system of the laser depilation apparatus in the present embodiment. Reference numeral 20 denotes a controller for controlling the whole apparatus. Reference numeral 21 denotes a laser source. For this laser source, an alexandrite laser source that emits a laser beam of a wavelength of 755 nm is used in the present embodiment. The laser beam emitted from the laser source 21 is deflected by the mirrors 22 and 23 in turn, then condensed by a lens 28, and made incident into the optical fiber 2. Reference numeral 24 is a scanner controller for controlling the activation of the motors 14a and 14b. Namely, a control signal from the controller 24 is transmitted to the scanner section 11 through a connector 5 and a cable 4 to activate the motors 14a and 14b, thus swinging the mirrors 13a and 13b respectively. Reference numeral 25 denote an image processing section for processing an image (thermogram) taken by the thermograph 6 to detect the positions of hair follicles, or pores in the skin, and the sizes (diameters) thereof.

A description will be made below on the method of detecting the position and size of each follicle using the thermogram produced by the thermograph 6.

In a laser depilation procedure, a laser beam of wavelengths likely to be absorbed into melanin is irradiated to the skin of a patient. Heat energy stemming from the laser beam absorbed and accumulated into the melanin is radiated to hair roots. The hair roots are thus cauterized for depilation. A region containing a larger amount of melanin absorbs a larger amount of heat energy stemming from a laser beam. The temperature of the region therefore rises temporarily. Melanin is distributed into the epidermis, hair follicles, and hair roots (hair). The distribution density of melanin in the hair roots is much higher than those in the epidermis and hair follicles. A larger amount of energy is therefore absorbed into the hair roots.

In general, a larger amount of melanin is accumulated in the periphery of the roots of thick hairs. When a laser beam is irradiated, the roots of thick hairs hold a larger amount of heat than the roots of thin hairs do. From this viewpoint, a laser beam of low power (of a level not damaging the epidermis) is diffused and irradiated in advance as a laser beam used to detect the positions of hair follicles into a predetermined range in the skin surface to be irradiated with a laser beam for depilation. The thermograph 6 is then used to record the distribution of temperatures in the range. Points indicating high temperatures are distinguished based on the record, whereby the positions of hair roots, that is, the positions of hair follicles can be specified. The thickness of each hair root, that is, the size of each hair follicle can be detected by measuring the area of the center of each of the points indicating the high temperatures.

Figure 4:
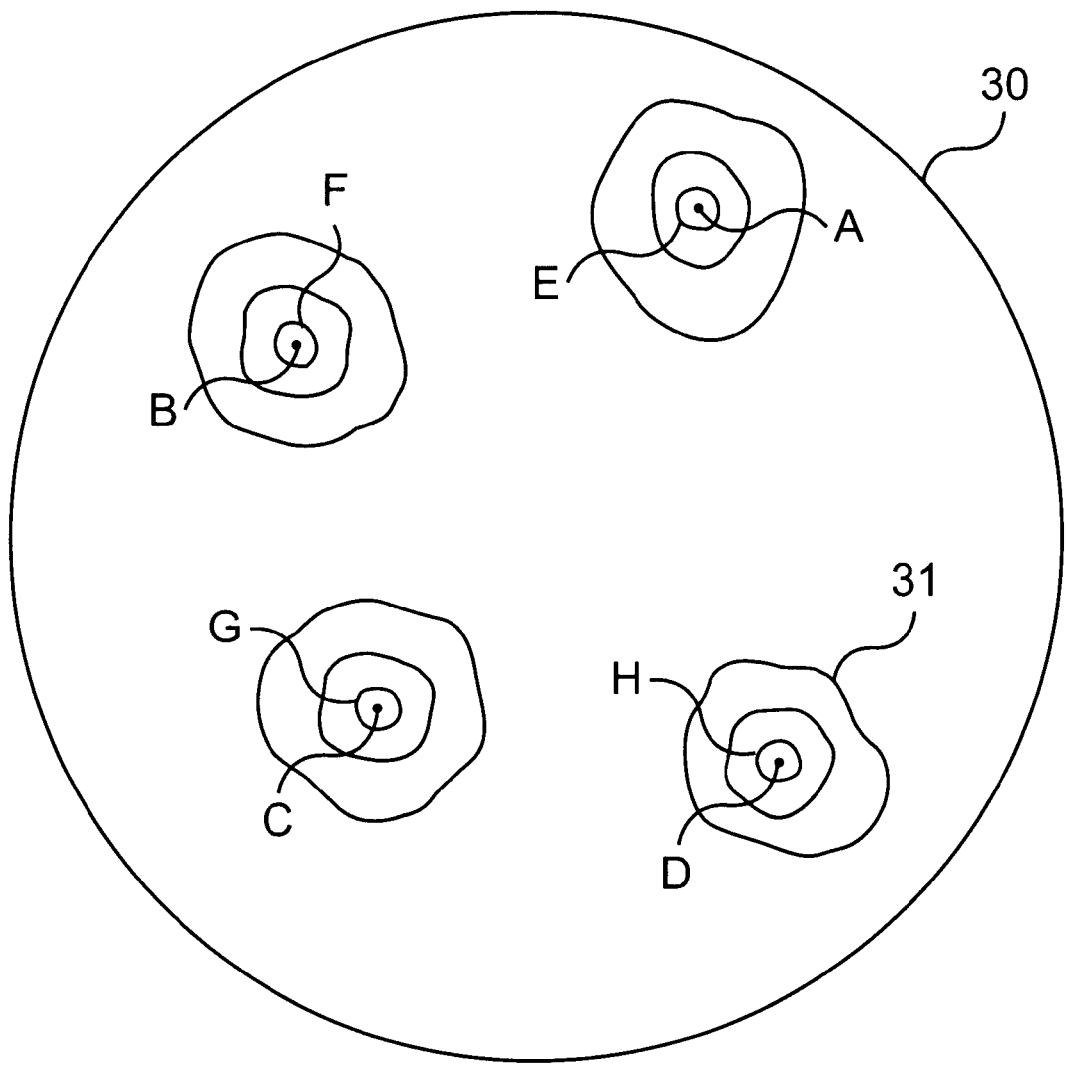
FIG. 4 is a schematic view of a distribution of temperatures on a skin irradiated with a laser beam.

FIG. 4 schematically shows a temperature distribution provided by the image processing section 25 which processes a thermogram produced by the thermograph 6. Reference numeral 30 denotes a laser-irradiated range. Reference numeral 31 denotes isotherms. Inmost isotherms 31 indicate the highest temperature. In this case, centers A, B, C, and D of ranges delineated with the inmost isotherms 31 are detected as the positions of hair follicles (positions of hair roots). The sizes E, F, G, and H of hair follicles (thicnesses of hair roots) at the positions are detected based on the areas of the center isothermal points.

When the thermograph 6 is employed, the timing of producing a thermogram preferably coincides with a time instant within a heat damping time of hair roots after a laser beam is irradiated. When a laser beam is irradiated to a target (melanin in this case), the distribution of temperatures in a zone centered on the target is observed as a Gaussian distribution whose width is determined with the diameter of the zone. In relation to the Gaussian distribution, the heat damping time is interpreted as the time required until the center temperature of the Gaussian distribution decreases to 50% thereof.

In general, the heat damping time of melanin falls within a range of approximately 10 nsec to 1 $\mu$sec, and the heat damping time of hair roots whose diameters range from 200 to 400 $\mu$m falls within a range of approximately 40 msec to 100 msec. After a laser beam is irradiated to a target, the temperature of melanin rapidly rises until the melanin enters its heat damping time. After the heat damping time elapses, the temperature of the melanin rises slowly, though heat is radiated from the melanin. At this time, heat energy radiated from the melanin is propagated to hair roots. The temperature of the hair roots therefore rapidly rises until the hair roots enter their heat damping time. Consequently, while the hair roots are spending their heat damping time, the temperature of the hair roots becomes different from the temperature of the surroundings. When the heat damping time of hair roots elapses, a temperature rise at the hair roots is suppressed and heat is conducted to the surroundings at the same time. For this reason, when too much time has passed after the heat damping time of hair roots elapses, a temperature difference between the hair follicles and their surroundings is hardly observed. It becomes therefore hard to detect the hair follicles.

The positions and sizes of hair follicles may also be detected as described below. That is to say, for example, a CCD camera sensitive to a visible region may be substituted for a camera 6a designed for thermography. The CCD camera is used to image the real state of the skin to which a laser beam is irradiated. The positions of hair follicles and the sizes thereof are detected based on colors or shapes observed from the image. Alternatively, light characteristic of emitting fluorescence when reacting on melanin may be irradiated to the skin. Otherwise, a fluorescent that reacts on melanin and is harmless to a living body may be administered in advance. Thereafter, the fluorescent reacting on melanin is imaged, and the positions of hair follicles and the sizes thereof are detected based on the emitted state of fluorescence.

Next, actions to be performed for laser depilation using the laser depilation apparatus constructed as above will be described. Before irradiating a laser beam, an operator shaves the skin of a patient in a range to be depilated and applies a cooling gel or the like to the skin. Thereafter, various kinds of setting for the apparatus are made using the control panel 7. The pole 17 of the hand-piece unit 3 is abutted on the skin so that a region to be depilated come under the head section 12. In this state, the hand-piece unit 3 is stabilized. The operator then presses a switch for instructing detection of the positions of hair follicles, which is not shown, located on the control panel 7.

When the switch is pressed, the controller 20 drives the motor 16 to insert the lens 15 onto the optical path of a laser beam. The controller 20 then drives the laser source 21 to emit a laser beam of low power (about one twentieth to one hundredth of the power used for depilation) as the laser beam used for detecting the positions of hair follicles. In general, the power of a laser beam used for depilation falls within a range of 10 to 40 $J/cm^2$. The power of a laser beam used for detecting the positions of hair follicles preferably falls within a range of 0.1 to 2 $J/cm^2$.

The a laser beam emitted from the laser source 21, which is to be used to detect the positions of hair follicles, is delivered to the hand-piece unit 3 through the fiber 2. The laser beam emitted from the fiber 2 is narrowed to have diameters ranging from 1 to 2 mm through the lens 10. The laser beam to be used for the detection is then diffused through the lens 15 and irradiated comprehensively to a region having a diameter of about 20 mm. At this time, the mirrors 13a and 13b are initialized to lie in their original positions.

When a laser beam is irradiated to the skin, heat energy stemming from the laser beam is, as mentioned above, accumulated in melanin. The temperature of hair roots becomes different from that of the surroundings. The region irradiated with the laser beam for detection is imaged using the thermograph 6 at a time instant within the heat damping time of hair roots. Information of a temperature distribution is produced by the image processing section 25. The positions of hair follicles and the sizes thereof are detected based on the temperature distribution information. The positions of hair follicles are indicated with coordinates. The position information and the information of the sizes at the positions are stored in the controller 20.

When the image processing section 25 completes detection, the controller 20 informs the operator of completion of detection of the positions of hair follicles using a monitor, which is not shown, of the control panel 7. At the same time, the lens 15 is withdrawn from the laser optical path in order to enable scanning with a laser beam whose diameters range from 1 to 2 mm.

The operator presses the foot switch 8 while holding the hand-piece unit 3, and thus inputs a laser beam irradiation command to the apparatus. When the command signal is input, the scanner controller 24 drives the motors 14a and 14b according to the stored position information. The controller 20 controls the timing of emitting a laser beam from the laser source 21. In the case shown in FIG. 4, first, the scanner controller 24 adjusts the angles of the mirrors 13a and 13b so that a laser beam can be irradiated to the position A of a hair follicle. The controller 20 causes the laser source 21 to emit a laser beam according to the timing of the angles having been adjusted. Thereafter, the angles of the mirrors 13a and 13b are adjusted so that a laser beam can be irradiated to the position B of a hair follicle. This sequence is repeated relative to the positions C and D of hair follicles. Emission of a laser beam and scanning with the laser beam are thus controlled, whereby a laser beam is irradiated selectively to the positions A to D of hair follicles. Consequently, the damage to surrounding tissues of the hair follicles can be alleviated.

At this time, the controller 20 controls driving of the laser source 21 so that the position of each hair follicle can be irradiated under optimal irradiation conditions that are varied depending on the size of each follicle (thickness of each hair root). The irradiation conditions include the irradiation power of a laser beam and the irradiation time thereof.

A description will be made on the irradiation power of a laser beam and the irradiation time thereof dependent on the size of a hair follicle (thickness of a hair root). The principles of laser depilation lie in that: a laser beam is absorbed into melanin present around hair roots; and accumulated heat energy is propagated to the hair roots and thus cauterizes the hair roots. At this time, the laser beam must be irradiated within a time longer than the heat damping times of melanin and the epidermis respectively but shorter than the heat damping time of hair roots. Thus, energy whose amount is so moderate as not to destroy melanin or the epidermis but large enough to cauterize hair roots must be provided within the time. The heat damping time of melanin falls within a range of approximately 10 nsec to 1 $\mu$sec, that of the epidermis falls within a range of 3 to 10 msec, and that of hair roots falls within a range of approximately 40 msec to 100 msec. However, the heat damping time varies depending on the thickness of a hair root. If the laser irradiation time were longer than the heat damping time of hair roots, energy would be diffused to the surroundings, which leads to the deteriorated effect of destroying hair roots. For this reason, the laser irradiation time should be adjusted within the range of 10 to 40 msec. For efficiently achieving depilation without inviting a temperature rise in the skin, a laser beam of power dependent on the thickness of a hair root must be irradiated. The power of a laser beam and the irradiation time thereof optimal to the thickness of a hair root should therefore be obtained quantitatively in advance. This data is used to determine the power of a laser beam for each hair root.

The present invention has been described on the assumption that a laser beam is irradiated selectively to each of the positions of hair follicles. The present invention can be implemented in a case where comprehensive irradiation is adopted. The comprehensive irradiation is such that: no scanner mechanism is included; and a laser beam whose diameters range from 10 to 20 mm is irradiated in order to cauterize all the hair roots within the irradiated region. Even in this case, the apparatus of the present embodiment detects the thickness of each hair root within the irradiated region and automatically optimizes irradiation conditions for a laser beam according to the information. Consequently, even an operator having a little experience can efficiently achieve depilation while suppressing the damage to the skin subjected to depilation. In other words, in the case of the comprehensive irradiation, the power of a laser beam and the irradiation time thereof are set relative to the thickest hair root within each irradiated region. A laser beam is therefore irradiated optimally at least for each region. When the apparatus of the present embodiment is used for comprehensive irradiation, a laser beam used for depilation should be irradiated with the lens 15 positioned in place.

The thicknesses of hairs may vary depending on the region of a body such as the arm or leg. When the thicknesses of hairs in the same region of a patient differ little, comprehensive irradiation may be more economically advantageous because the apparatus need not have a mechanism thereof operated in a complex manner.

Furthermore, a mechanism may be included for switching a mode in which a laser beam is irradiated selectively and a mode in which a laser beam is irradiated comprehensively. In this case, an operator can select between the modes according to different purposes, for example, by using a selection switch provided on the control panel 7. This leads to more efficient depilation.

The present invention may be embodied in other specific forms without departing from the spirit or essential characteristics thereof. For instance, although the alexandrite laser source is used in the above embodiment, it may be replaced with another laser source that can produce a laser beam of wavelengths which are likely to be absorbed into melanin and capable of reaching the melanin accumulated in the periphery of hair roots. Instances thereof are: a ruby laser source, a diode laser source, and the like.

In the above embodiment, the power of a laser beam for depilation is lowered when the laser beam is used as a laser beam for detecting the positions of hair follicles. Another laser beam may also be used for the detection of the positions of hair follicles.

The laser beam to be used for detecting the positions of hair follicles is diffused through the lens 15. Instead thereof, the laser beam may be irradiated in the form of a small spot to scan the entire range to be irradiated (detected).

In the above embodiment, the region for detection of positions of hair follicles (namely, the laser-irradiated region with a laser beam used for the detection of positions of hair follicles, the region imaged by the camera 6a) is determined to be identical to the range to be irradiated with a laser beam for depilation. Although they may not be identical, the range for the detection of the positions of hair follicles must include at least the range to be irradiated with a depilation laser beam.

Furthermore, to control a laser emission timing of the laser source 21, the laser source 21 itself may be controlled or a shutter not shown may be inserted/removed onto/from the optical path.

As mentioned above, according to the present invention, a laser beam can be irradiated selectively to only the positions to be depilated, so that the damage to surrounding tissues of the hair follicles can be alleviated and also depilation can be efficiently achieved. Laser irradiation conditions are appropriately determined according to the thickness of a hair, achieving more efficient depilation.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser depilation apparatus for performing depilation on a skin by irradiating the skin with a laser beam, the apparatus comprising:

first irradiation means including a laser source for emitting a laser beam for depilation and a light delivery optical system for delivering the depilation laser beam emitted from the laser source into a first predetermined range to irradiate the range;

detection means, including a CCD camera for forming an image of a surface of the skin within at least a first range;

an image processor for processing the image and detecting thickness of a hair follicle based on an amount of melanin existing along the hair follicle;

irradiation condition setting means for variably setting at least one of irradiation time of the depilation laser beam and irradiation power based on the detected hair follicle thickness; and control means for controlling the first irradiation means based on a setting set by the irradiation condition setting means.

2. The laser depilation apparatus according to claim 1, wherein the laser source includes one of an alexandrite laser source, a ruby laser source, and a diode laser source.

3. The laser depilation apparatus according to claim 1, wherein the image processor detects a position of the hair follicle based on the melanin existing along the hair follicle, and the control means controls the first irradiation means based on a position of the detected hair follicle.

4. The laser depilation apparatus according to claim 3, wherein the first irradiation means includes scanning means in the light delivery optical system, the scanning means causing the depilation laser beam formed into a small spot to scan the first range in a two-dimensional direction.

5. A laser depilation apparatus for performing depilation on a skin by irradiating the skin with a laser beam, the apparatus comprising:

first irradiation means including a laser source for emitting a laser beam for depilation and a light delivery optical system for delivering the depilation laser beam emitted from the laser source into a first predetermined range to irradiate the range;

second irradiation means for irradiating a second predetermined range including the first range with a laser beam used for detection, the detection laser beam reacting on melanin existing along a hair follicle and producing a temperature variation within the second range;

detection means including a thermograph used for detecting a distribution of temperature variations on the skin irradiated with the detection laser beam, for detecting a thickness of the hair follicle based on a signal output from the thermograph;

irradiation condition setting means for variably setting at least one of irradiation time of the depilation laser beam and irradiation power based on a detection result of the detection means; and control means for controlling the first irradiation means based on a setting set by the irradiation condition setting means.

6. The laser depilation apparatus according to claim 5, wherein the second irradiation means shares the laser source and the light delivery optical system with the first irradiation means, and irradiates the second range with a laser beam of lower power than power needed for depilation, the laser beam being used as the detection laser beam.

7. The laser depilation apparatus according to claim 6, wherein the second irradiation means emits the detection laser beam of low power that falls within a range of one twentieth to one hundredth of power of the depilation laser beam.

8. The laser depilation apparatus according to claim 6, wherein the second irradiation means includes a laser diffusion member that is removably laid on an optical path of the light delivery optical system during the detection.

* * * * *